United States Patent
Ozerov

(10) Patent No.: US 6,613,209 B2
(45) Date of Patent: Sep. 2, 2003

(54) TONER CHARACTERIZATION CELL

(75) Inventor: Alexander Borisovich Ozerov, Oakden (AU)

(73) Assignee: Research Laboratories of Australia Pty Ltd. (AU)

( * ) Notice: Subject to any disclaimer, the term of this patent is extended or adjusted under 35 U.S.C. 154(b) by 338 days.

(21) Appl. No.: 09/771,487

(22) Filed: Jan. 25, 2001

(65) Prior Publication Data

US 2001/0035352 A1 Nov. 1, 2001

(30) Foreign Application Priority Data

Jan. 28, 2000 (AU) .............................. PQ 5290

(51) Int. Cl.[7] ..................... G01N 27/447; G01N 27/453
(52) U.S. Cl. ..................... 204/450; 204/600; 356/344
(58) Field of Search ..................... 204/450, 600; 356/344

(56) References Cited

U.S. PATENT DOCUMENTS

| | | |
|---|---|---|
| 3,454,487 A | 7/1969 | Riddick |
| 3,764,512 A | 10/1973 | Greenwood et al. |
| 3,793,180 A | 2/1974 | Flower et al. |
| 3,909,380 A | 9/1975 | Day et al. |
| 4,046,667 A | 9/1977 | Goetz |
| 4,113,596 A * | 9/1978 | Treille et al. ............ 204/549 |
| 4,497,208 A | 2/1985 | Oja et al. |
| 4,679,439 A | 7/1987 | Culkin |
| 4,928,065 A | 5/1990 | Lane et al. |
| 5,059,909 A | 10/1991 | O'Brien |
| 5,848,322 A | 12/1998 | Chen et al. |

FOREIGN PATENT DOCUMENTS

WO  9930141  *  6/1999

* cited by examiner

Primary Examiner—Nam Nguyen
Assistant Examiner—Alex Noguerola
(74) Attorney, Agent, or Firm—Brown, Martin, Haller & McClain LLP

(57) ABSTRACT

A toner characterization cell used to determine characteristics of insoluble particles in a liquid medium. First and second electrode are spaced apart and an electric field is applied between the electrodes and a displacement current is measured. Optical density measuring devices measure the change in optical density in the cell adjacent each electrode. The characteristics are determined from the displacement current and the change in optical density. The characterizing feature may be particle mobility. The invention also relates to a method of determining the characteristics.

33 Claims, 4 Drawing Sheets

TONER CHARACTERIZATION CELL

FIELD OF THE INVENTION

The present invention relates generally to electrophoresis apparatus, and more specifically a method and apparatus for the measurement of characteristics such as electrophoretic mobility of particles suspended in a low-permittivity non-aqueous liquid medium. The invention will be discussed in relation to its relevance to electrostatographic printing or copying process parameters but is not so restricted as it also relates to other situations where characteristics such as mobility of particles under the influence of an electric field are of interest.

BACKGROUND OF THE INVENTION

It is well known that the electrical properties of liquid toners used in electostatography significantly influence the quality of a printed image; the most important electrical characteristics of conventional liquid toners are known to be conductivity, electrophoretic mobility and charge to mass ratio. Although the physical background of these characteristics is understood, accurate and reliable methods for measuring these properties are limited.

The term zeta potential is understood in colloidal chemistry as an indicator of the electrophoretic mobility of particulate matter colloidally suspended or dispersed in a fluid medium. The electrophoretic mobility, in turn, is an indication of the velocity of the particles through the solution due to the effect of an applied electric field.

The stability of a particle suspended in a bulk medium is related to the zeta potential of the particle. Stable particles remain dispersed whereas unstable particles tend to agglomerate and eventually precipitate out of the solution. The higher the zeta potential, the more stable the system is since highly charged particles repel one another and remain dispersed.

In the field of liquid electrostatographic printing and copying, development of a latent image takes place at high speeds, which requires, in one form, that a large amount of uniformly characteristic liquid developer marking particles be supplied to the latent image surface as uniformly as possible to produce a high quality image without any variations in the development thereof.

Therefore, the measurement of the mobility of electrostatic particles dispersed in a dielectric medium under the influence of externally applied electric fields is useful for allowing the assessment of liquid toner sensitivity and at the same time providing a means for analysis of the behaviour of liquid toners as well as their individual constituents.

Various prior art apparatus and means have been utilised to measure the zeta potentials of colloidal particles suspended in a liquid medium. U.S. Pat. No. 3,454,487 to Riddick discloses an electrophoresis apparatus, wherein the electrophoretic mobility, i.e. the velocity of the particles per unit field strength, is measured in an electrophoretic cell which consists of sample receiving chambers connected by a liquid-flow communication passageway.

This measurement is performed utilising an ocular micrometer or distance scale which is inserted into the eyepiece of a microscope. The particles are timed as they cross a fixed distance in the observation chamber of the electrophoretic cell under a D.C. electric field of known strength.

In U.S. Pat. No. 3,764,512 to Greenwood et al. discloses an apparatus utilising a coherent light beam from a laser which is caused to intermittently scan a path located on the stationary layer of an electrophoresis chamber by means of a mirror galvanometer at a rate equal to the migration rate of the particles in the chamber. The operator views the migrating particles in the chamber through a microscope and simultaneously adjusts the scanning rate of the mirror galvanometer by adjusting a potentiometer in the galvanometer control circuit until the scanning laser beam appears to visually track the migrating particles as viewed through the microscope. Via appropriate scaling circuitry interacting with the galvanometer drive circuit and the circuit supplying the voltage drop across the chamber, a value for electrophoretic mobility or zeta potential may automatically be displayed through suitable means, such as an electronically operated digital readout.

In U.S. Pat. No. 3,793,180 to Flower et al. discloses a system capable of measuring zeta potential, particle size distribution, total charge density and other distribution functions of aqueous suspensions. A laser beam is provided in the instrument and is focused on the particles in the sample solution which are contained in an electrophoretic cell. A reticle or grating is positioned such that the reflection of the laser beam from the particles passes through the reticle to a photo-tube placed on the other side of the reticle. Then, as the particles move through the solution the photo-tube is intermittently illuminated through the reticle and, as a result, generates a train of electric pulses whose frequency is directly proportional to the velocity of the particles. Since the frequency of the electrical signal is a measurement of the particle velocity, it is also a measure of zeta potential.

In U.S. Pat. No. 3,909,380 to Day, a television camera or other equivalent image sensor, such as a photosensitive array utilising a suitable lens system, observes the fluid within an electrophoresis cell which is illuminated by the cold light of a fiberoptic source in order to prevent the production of convection currents in the medium. The suspended particles are magnified by a microscope and the image is projected onto the monitor screen. A reference pattern is superimposed onto the monitor and the sweep speed of the reference pattern is then manually adjusted to match the speed of any single particle or group of particles on the monitor screen. The sweep speed of the reference pattern may then be converted to a zeta potential signal which must be corrected for the temperature of the sample.

In U.S. Pat. No. 4,046,667 to Goetz describes an electrophoresis chamber, a circuit for impressing a voltage across the chamber, a light beam to illuminate a portion of the chamber, and a microscope including an objective lens system and an eyepiece for viewing illuminated particles migrating relative to a suspending medium within the chamber under the influence of the applied voltage. Within the microscope, between the objective lens and the eyepiece, is a movable optical prism driven by a galvanometer, the drive circuit of which includes an adjustable potentiometer for controlling the rate and direction of movement of the optical prism.

A circuit connected to the galvanometer drive circuit and the circuit applying the voltage potential across the chamber are adapted to develop a signal proportional to the electrophoretic mobility or zeta potential of the migrating particles when the rate of movement of the optical prism is adjusted such that it cancels the transfer velocity of the migrating particles. The particles then appear stationary when observed through the eyepiece of the microscope.

The hereto disclosed prior art apparatus and means can be characterised as utilising direct methods in which to determine electrophoretic mobility, that is, electrophoretic mobility being a linear function of particle velocity, is therefore derived from direct measurement of actual said velocity; this requiring the liquid toner sample to be transparent or semi-transparent to the light beam of the sensing device. In contrast, there also exist techniques whereby indirect methods can be used in determining electrophoretic mobility. In these indirect methods, secondary effects caused by particle motion within the dispersion are used, processed and converted into mobility measurements, as taught by the following prior art examples.

In U.S. Pat. No. 4,679,439 to Culkin, there is described a method and apparatus for measuring the unsteady sedimentation potential of particles in a suspension comprising the insertion of a portion of the suspension of particles in a cell, the cell having a first and a second electrode. A speaker motor means is used to vibrate the cell and to accelerate the particles in suspension and allowing the measuring of the unsteady sedimentation potential of the particles across the first and second electrodes, the cell being vibrated at a frequency in the range between 0.0001 to 50 kHz.

In U.S. Pat No. 4,928,065 to Lane et al. describes a method and apparatus for classifying non-aqueous liquid suspensions of charged particles employing a large time-varying electric field applied to a suspension situated between capacitive test electrodes. A current waveform is produced that characterises the suspension with respect to critical properties including concentration, mobility, and plating tendencies of the charged particles suspended therein.

In U.S. Pat No. 5,848,322 to Chen et al. discloses an apparatus for determining charge density and mobility in a liquid solution having electrically charged particles therein. The apparatus includes an electrode and a dielectric member having a first surface situated opposite the electrode for providing a volume therebetween in which a sample of the liquid may be placed. A fixed bias voltage applied to the electrode to produce an electrical current flow through the liquid solution and the dielectric member. A device coupled to the dielectric member, measures the electrical current as a function of time to provide a measure of voltage decay across the liquid solution. The voltage decay corresponds to the charge density of the liquid solution.

In U.S. Pat No. 4,497,208 to Oja et al. discloses a method and apparatus for measuring the electro-kinetic properties of a liquid dispersion in which electrodes are placed in the liquid and an apparatus is provided for applying an alternating electrical potential to these electrodes. The electric field from this alternating potential acts upon the charged elements in the liquid, resulting in the generation of sound at the frequency of the applied electrical potential. By placing a conventional acoustic transducer in a spaced relationship to the electrodes, the acoustic signal is detected and measured. The amplitude of the acoustical signal will be a function of the electro-kinetic properties of the particles in the liquid. In its preferred form, the electrodes that are placed in the liquid have a spacial separation of one-half wave length, or odd integer multiples of half wave length of the sound which they generate. Coupled to the receiving transducer is a receiver that will amplify the signal to convenient levels.

In U.S. Pat. No. 5,059,909 to O'Brien also discloses a measurement device whereby the interaction of sound waves and electric fields in the fluid medium over a range of frequencies are used to obtain the particle size and zeta potential.

The presently preferred indirect electrophoretic mobility measurement is the so called electro-kinetic sonic amplitude (ESA) technique. This method however, uses very high frequency AC signals and relies to a great extent on a number of theoretical principles in order to convert the measured ESA signal into electrophoretic mobility values. It is difficult to directly apply the results of these high frequency measurements to the actual DC electrophoresis of liquid toner marking particles, especially in relation to image development in a typical electrostatographic process.

It can be realised from all the above prior art discussion that the requirements for the measurement of the mobility of marking particles in a liquid of high viscosity, in the order of up to 10,000 mPa·s, and of high solids content, of up to 60% by weight, for electrostatographic methods can not be readily and accurately determined by any of the hitherto described art. The above described apparatus and methods, referred to herein as direct measurement techniques, have been primarily designed for liquid mediums which are to a degree transparent or semi-transparent such that an observer or means for detecting the movement of individual particles is possible, or utilise techniques and derive results which cannot be readily applied to electrostatographic development processes being currently disclosed. Also, these prior art methods are normally associated with liquids which can be defined in terms of conventional electrostatography as low viscosity liquids. The prior art does not fulfil the requirement of duplicating real electrographic process parameters such as for example, utilising actual gap dimensions and appropriate electric field strengths.

Further, it is well known that marking particle dispersions of "working strength" dilution, that is, particle dispersions with approximately 0.5 to 2% by weight solids content, require in most cases further dilution of as much as 100:1 to allow measurements to be undertaken in most prior art apparatus of the type described.

There is a need therefore, to be able to characterise liquid toners which have a range of viscosity, and a range of concentration without the need for dilution, and in which the replication of real conditions, such as actual gap dimensions, associated with printing or copying system are realised.

It is an object of the instant invention to provide an apparatus and method whereby synchronous optical and electrical measurements, which can provide complimentary information about a particles mobility and charge as well as other specific characterisation of working strength marking particle dispersions, can be undertaken, the dispersions of marking particles consisting of liquids having a viscosity, in the order of up to 10,000 mPa·s, and a solids content of the marking particles, of up to 60% by weight therein. Such a marking particle dispersions having a total viscosity in the order of up to 500,000 mPa·s.

The present invention describes an apparatus and method that allows synchronous electrical and optical measurements of the mobility of concentrated particles suspended in a liquid medium of high viscosity.

BRIEF DESCRIPTION OF THE INVENTION

The present invention discloses novel apparatus and method for characterisation of pertinent properties of low permittivity non-aqueous liquid dispersions of charged particles, including the electrophoretic mobility, toner compaction and other pertinent electrical parameters deemed of importance to liquid toners in the art of electrostatography and which significantly influence the quality of a printed image.

In one form therefore the invention is said to reside in a toner characterisation cell adapted to determine characteristics of insoluble particles in a liquid medium, the cell including a first electrode and a second electrode spaced apart by a selected gap, means to provide an electric field between the first electrode and the second electrode, means to measure a displacement current between the first electrode and the second electrode, first and second optical density measuring devices adapted to measure the change in optical density in the cell adjacent each electrode, and means to determine the characteristics from the displacement current and the change in optical density.

Preferably the first electrode and the second electrode are substantially transparent or translucent. To allow for transparency or translucency while still acting as an electrode the electrodes may be coated with a transparent conductive material. For instance the transparent conductive material may be conductive indium tin oxide. The indium tin oxide may be coated on a front surface of the electrodes.

The electrodes may be substantially planar and may be formed from glass plates.

Where the cell is used for the characterisation of toners and the like in which the gap is substantial there may be used a wall arrangement to contain the toner between the electrodes. The gap between the electrodes may be in the range of 1 $\mu$m to 10 mm.

There may be used micrometer means to adjust and measure the gap between the first electrode and the second electrode.

The optical density measuring devices may each comprise an infra-red emitting diode and phototransistor pair.

The composition which comprises the insoluble particle in a liquid medium characterised according to this invention may be a liquid toner for electrostatography or an ink or other particle suspension. Such a liquid toner or ink may be of low or high viscosity.

In particular the invention is useful for the characterisation of insoluble particle suspensions in a liquid medium where there is to be an electric field applied, particularly a high voltage electric field.

In an alternative form the invention may be said to reside in a cell including a base, a tool post mounted to the base, a longitudinal track on the tool post, a traveller on the track, a first electrode assembly mounted to the base, a second electrode assembly mounted to the traveller, displacement adjustment means between the post and the traveller whereby the distance between the first electrode assembly and the second electrode assembly may be adjusted, a first optical density measuring device associated with the first electrode assembly, a second optical density measuring device associated with the second electrode, means to provide an electric field between the first electrode and the second electrode, means to determine a displacement current between the first electrode and the second electrode, and means to calculate electrophoretic characteristics of a suspension of particles in a highly viscous dispersion placed between the first and second electrodes from the displacement current and the change in optical density at the first and/or the second electrodes determined with the optical density measuring devices.

In an alternative form the invention may be said to reside in a method of determining the characteristics of particles in a dispersion, a method including the steps of causing particles to move in response to an applied electric field between a first electrode and a second electrode spaced apart by a selected distance, determining a displacement current caused by the particles so moved, determining by optical means particle compaction or diffusion due to the particle movement adjacent the first and/or second electrodes and determining the characteristics from the displacement current and the change in particle compaction or diffusion.

In an alternative form the invention may be said to reside in a method of determining the mobility of particles in a liquid dispersion, the method including the steps of placing a selected amount of the liquid with the particles suspended therein on to a first planar transparent electrode, moving a second planar transparent electrode adjacent the first electrode such that they are spaced apart by a selected gap, applying a selected voltage to one of the electrodes to cause particles to move electrophoretically between the first electrode and the second electrode, measuring a displacement current caused by the particles so moved, determining by optical means particle compaction or diffusion due to the particle movement adjacent the first and/or second electrode and calculating the particle mobility from the displacement current and the observed changes in optical density.

The data collected from both the optical means such as phototransistor detectors and the displacement current measuring means such as power supply and current sensing means, may be fed to a computer allowing mathematical manipulation of the data and therefore permitting characterisation of the liquid toner dispersion including determination of particle mobility and the compaction ability of the marking particles within said dispersion.

The device and method of the present invention may be used in a laboratory for the characterisation of insoluble particle suspensions in a liquid media in either development or manufacturing settings. Alternatively the device and method of the present invention may be used for process control, built into for instance a electrostatographic printing device, to monitor the use of toners or inks, for instance, during recycling of toners, and as such could incorporate a particle suspension flow through means.

DETAILED DESCRIPTION OF THE INVENTION

In conventional liquid electrostatographic printing and copying, the characterisation of dispersed electrostatic particles by means of electrophoretic analysis plays an important role in predicting the quality of liquid developers as well as allowing the replication of real development condition in such a system.

Electrokinetic potential is understood in colloidal chemistry as an indication of the electrophoretic mobility of particulate matter suspended or dispersed in a fluid suspending medium, and as an indication of the velocity or migration of a colloid particle through a fluid suspending medium under the effect of an applied electric field. It is understood that the suspended particles are considered electrically neutral, in the sense that they appear to have little if any activity with regard to an electric charge measuring means, but have an electrically charged double layer of electrons at the surface of the particles. That is, with suspended particulate material in a fluid medium, each particle is surrounded by a double layer of electrical or electrostatic charges, the inner layer of which may be considered immediately adjacent or fixed to the particle, while the outer layer of charges may relate more to constituents or characteristics of the suspending medium and to posses a charge opposite to that of the inner layer.

The net electric charge surrounding the particle, therefore, may be substantially zero with a resulting electric neutrality of the particle, yet as is now understood, such double layer of electric charges or "diffuse double layer" produces a colloidal and or interfacial effect on the mobility or occluding tendency of the particles and or the electrokinetic potential or electrophoretic mobility thereof in the suspending medium. The electrokinetic potential or zeta potential may be conveniently considered as the electrical potential drop across the diffuse double layer of electric charges at the interface between the surface of the particle and the bulk of the suspending medium.

The measurement of the zeta potential then gives an indication and useful information with regard to the electrophoretic or electrokinetic movement or migration or mobility of colloidal or other larger dispersed particles through a suspending medium.

In general, a liquid toner for developing electrostatic images is prepared by dispersing an inorganic or organic colorant such as iron oxide, carbon black, nigrosine, phthalocyanine blue, benzidine yellow, quinacridone pink and the like into a non-conductive dielectric liquid vehicle which may contain dissolved or dispersed therein synthetic or naturally occurring polymers such as acrylics and their copolymers, alkyds, rosins, rosin esters, epoxies, polyvinyl acetate, styrene-butadiene, cyclised rubber, ethylene vinyl acetate copolymers, polyethylene, etc. Additionally, to impart or enhance an electrostatic charge on such dispersed particles, additives known as charge directors or charge control agents may be included. Such materials can be metallic soaps, fatty acids or lecithin.

It can be appreciated from the foregoing therefore, that the immediate response of such a liquid toner to an externally applied electric field within an electrophoretic cell arrangement, is that although all charged species in the liquid toner dispersion will react, it is the highly mobile species that are rapidly swept to an oppositely charged electrode. As the spatial displacement of any charge constitutes an electric current, a significant initial current is therefore measured, without any significant toner marking particle deposition or movement. The magnitude of this current is dependent upon the motion of these highly mobile species, since they are the major charge carriers in the liquid toner dispersion. Once these charge carriers are swept from the liquid, the less mobile toner marking particles become the major contributors of charge transfer, resulting in a drop of the measured current but an increase in the deposition of marking particles on the oppositely charged electrode.

It is to be understood that current transient readings enable the measurement of the total displacement current created by all individual charge carriers. Due to the fact that there always exists a velocity distribution between the charged species experiencing electrophoretic migration, it often becomes difficult to distinguish the contribution of toner marking particles from other charge carriers.

It can be readily acknowledged therefore, the requirement to simultaneously capture both optical and electrical displacements which provide complimentary information about a particles mobility and charge leading to the specific characterisation of a marking particle dispersions as it relates to electrostatic latent image development.

In the case where the liquid toner sample is not of a transparent nature or of a useable viscosity, the prior art methods require the toner sample to be transparent to light and therefore would need to be diluted to carry out any particle mobility measurement. The act of dilution leads to mechanical and electrical sample changes which in turn affect the behaviour of the sample under an electric field and therefore giving an erroneous result which would not be indicative of the liquid toners performance in an electrographic printing or copying system.

Further, some examples of liquid toners can be characterised by particle mobility, of about $10^{-11}$ to $10^{-12}$ $m^2/V/s$, that is, substantially lower than that of conventional liquid toners and approaching the detectable limits of most mobility measuring methods. Also, the printing or copying process electric fields associated with these new types of liquid toners are normally greater than $10^6$ V/m; high fields are required to compensate for the low electrophoretic mobility of the particles within these liquid toners. The current invention provides a means whereby undiluted liquid toners of the type described can be easily characterised.

For an understanding of the features of the present invention, reference is made to the drawings, wherein like reference numerals have been used throughout to designate identical elements. It will become apparent from the following discussion that the apparatus of the present invention may be modified to suit a wide variety of embodiments; thus although the present invention will be described in connection with a preferred environment thereof, it will be understood that the description of the invention is not intended to limit the invention to this preferred environment and or embodiment. Indeed the description is intended to cover all alternatives, modifications, and equivalents as may be included within the spirit and scope of the invention as defined by the appended claims of the present invention.

BRIEF DESCRIPTION OF THE DRAWINGS

With reference to FIG. 1, one embodiment of an electrophoretic cell device is shown for practising the invention The device consists of a tool post 1 attached to a base 9. Longitudinal track 3 is attached vertically along inside face of tool post 1. Traveller 4 being attached to longitudinal track 3 and therefore allowing precise up-and-down movement of said traveller 4. Micrometer 8, attached to tool post 1 facilitates incremental movement of traveller 4 thus allowing the setting of accurate cell electrode gaps within cell electrode housing 5. An upper infra-red emitting diode and combined spectrally matched silicon phototransistor detector 6 attached to upper sensor mount 12 allows measurement of top electrode toner movement, deposition, diffusion or compaction. Upper sensor mount 12 is attached to upper cell housing 13, by upper bracket 14. Fine adjustment of upper phototransistor detector 6 is possible by means of upper sensor adjustor 15. A lower infra-red emitting diode and combined spectrally matched silicon phototransistor detector 10 attached to lower sensor mount 11 allows measurement of lower electrode toner movement, deposition, diffusion or compaction. Clamp 2 on top side face of tool post 1 allows traveller 4 to be held securely in place while cell electrode housing 5 is being assembled or disassembled. A mechanical stop arrangement 7 allows for coarse control of cell electrode gaps within cell electrode housing 5 of traveller 4, and easy separation of cell electrode housing 5 from base support 9.

Figure 2:
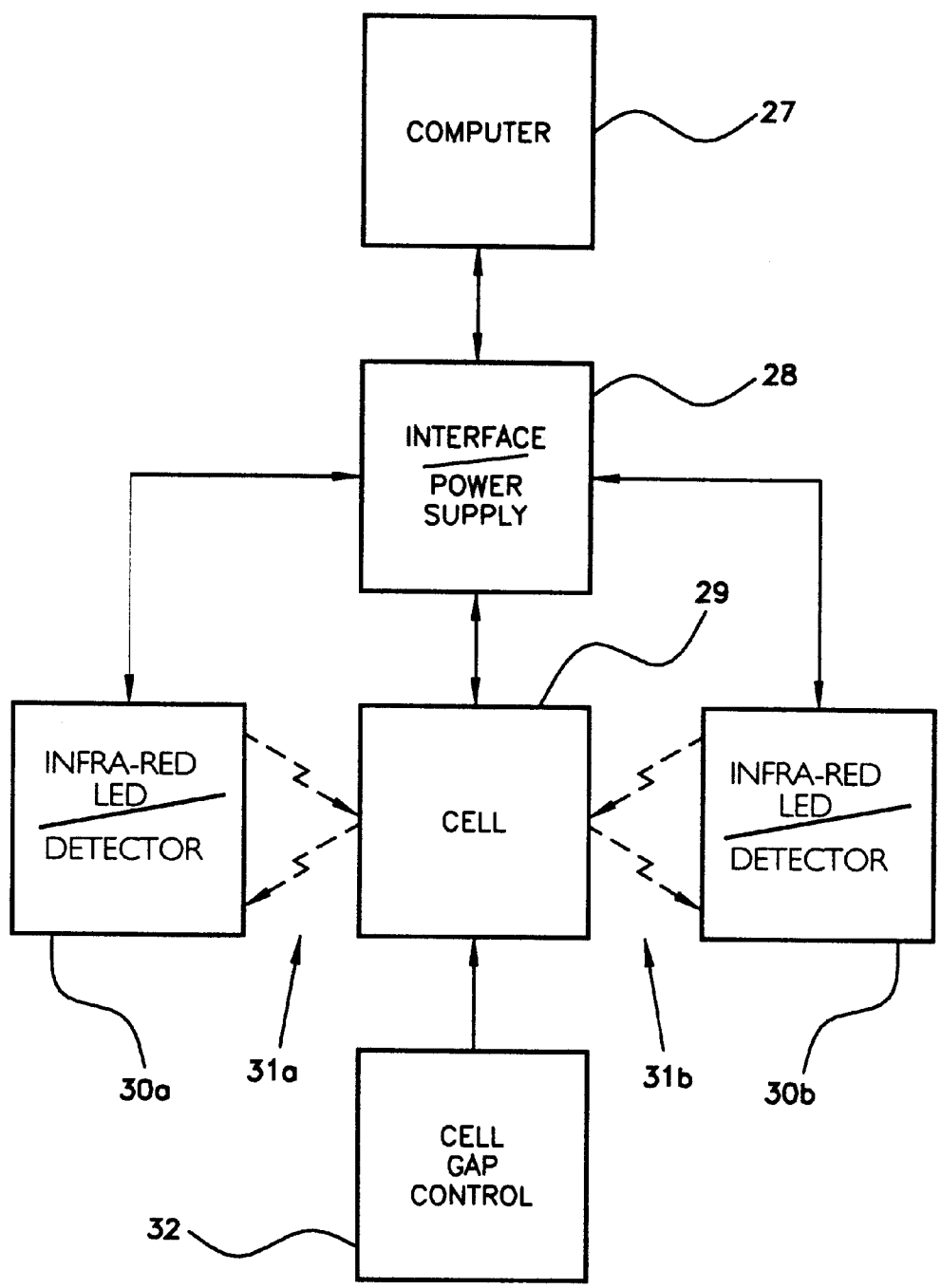
FIG. 2 shows a block diagram representation of the concept of the invention on a functional basis.

With reference now to FIG. 2, which shows a block diagram representation of the concept of the invention on a functional basis, cell 29 is connected to interface/power supply 28. Voltage and wave function output of interface/power supply 28 is controlled by computer 27. Infra-red LED 30a and infra-red LED 30b emit light 31a and 31b into cell 29, which is reflected into phototransistor detector 30a and phototransistor detector 30b, of which output signals are collected by Interface/power supply 28. The cell gap is maintained and controlled by cell gap control means 32. Any displacement current through cell 29 is detected by Interface/power supply 28. All parameters are collected by computer 27, said computer 27 controlling the operation of the electrophoretic cell as well as mathematically manipulating the collected input for graphical analysis.

Figure 3:
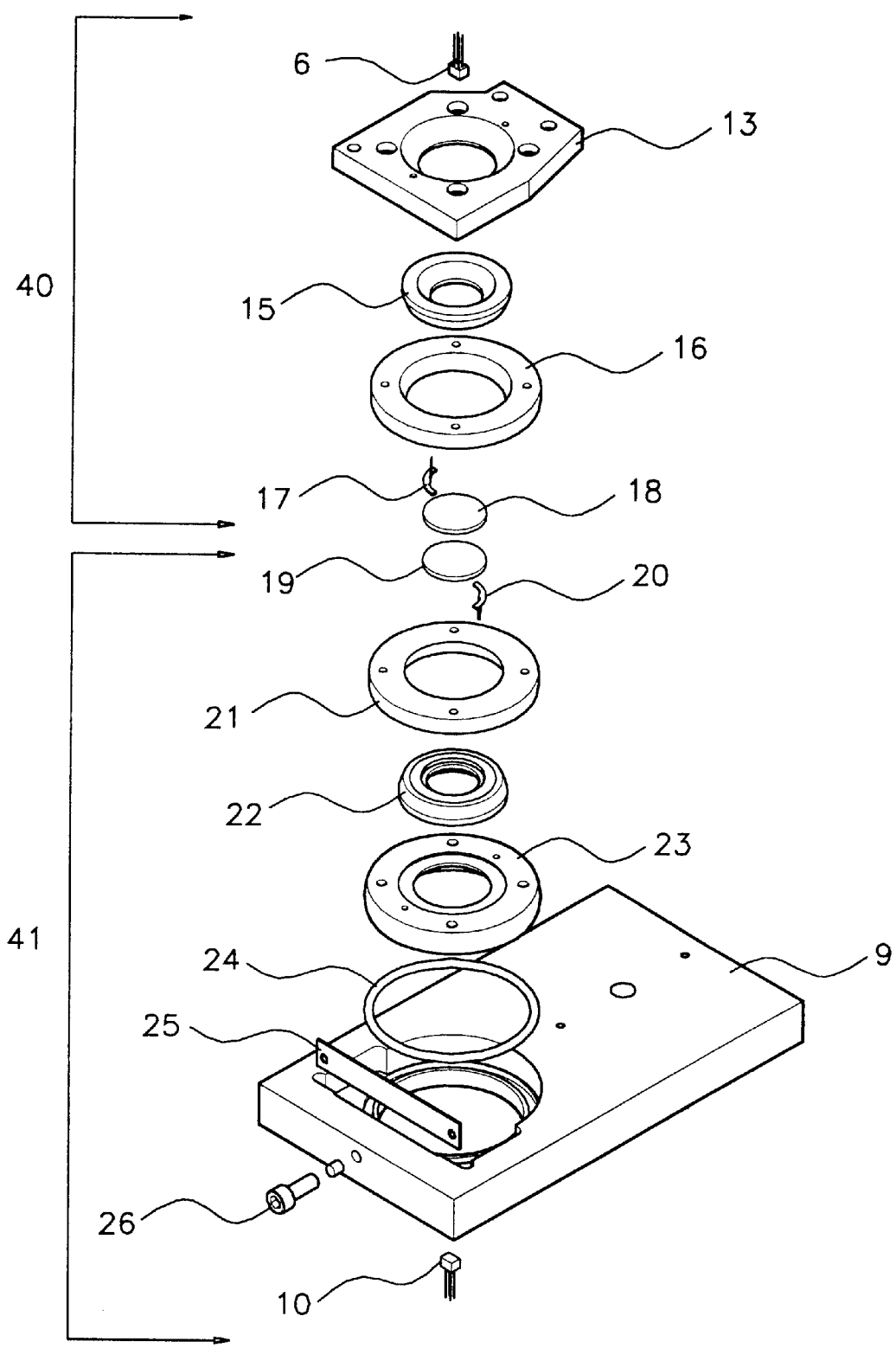
FIG. 3 represents a detailed view of the cell electrode housing of the embodiment of FIG. 1.

Turning now to FIG. 3, representing a detailed view of the cell electrode housing assembly, consisting of an upper cell assembly section 40 and a lower cell assembly section 41. Firstly, referring to lower cell assembly 41, base member 9, in which a recess accommodates a lower electrode assembly base 23 having a silicone "O" ring 24 therebetween. Lower electrode assembly base 23 being maintained and fixed in recess of base plate 9 by leaf spring 25 and locking screw 26. Lower transparent electrode 19 is constructed of glass coated with a thin layer of indium tin oxide on the inner surface thus forming a transparent and electrically conducting surface to which an electrical connector 20 is attached. Lower electrode 19 is attached to lower insulator 22, which is held to lower electrode assembly base 23 by lower clamp ring 21.

Referring now to the upper cell assembly 40, consisting of an upper electrode assembly base 13. An upper transparent electrode 18 is constructed of glass coated with a thin layer of indium tin oxide on the inner surface thus forming a transparent and electrically conducting surface to which an electrical connector 17 is attached. Upper electrode 18 is attached to upper insulator 15, which is held to upper electrode assembly base 13 by upper clamp ring 16.

Figure 1:
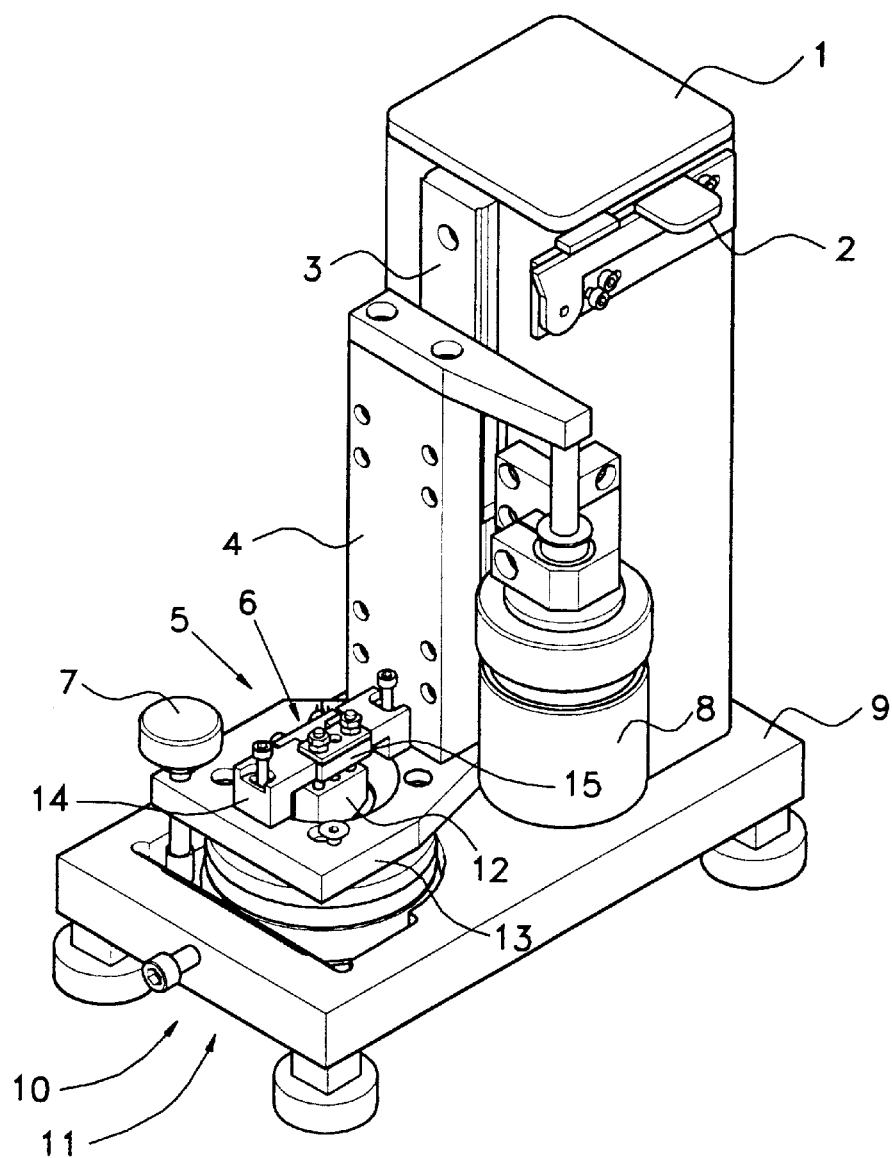
FIG. 1 shows a view of one embodiment of the electrophoretic cell device of the present invention.

An upper gallium arsenide infra-red emitting diode and a spectrally matched silicon phototransistor detector mounted side by side on parallel axes and housed in a black plastic moulding 6 to reduce ambient light noise, is located at the top of upper cell assembly 40. The photosensor responds to radiation only when a reflective object passes within its field of view. By adjusting upper sensor adjustor 15 (FIG. 1), the upper infra-red emitting diode and combined spectrally matched silicon phototransistor detector 6 is placed against the outer surface of upper glass electrode 18. A lower infra-red emitting diode and combined spectrally matched silicon phototransistor 10, is located at the bottom of lower cell assembly 41. By adjusting lower sensor adjustor (not shown), the lower infra-red emitting diode and combined spectrally matched silicon phototransistor detector 10 is placed against the outer surface of lower glass electrode 19. Both infra-red emitting diode and combined spectrally matched silicon phototransistor are adjusted such that the focal plane coincides with the maximum phototransistor detector current, said focal plane also coinciding with the inner surface of appropriate conductive glass electrode. It will be understood that the addition of extra optical systems would allow the range extension of said focal plane.

The above disclosed apparatus can be operated with the following procedure. Upper cell assembly 40 and lower cell assembly 41 are urged together by lowering traveller 4. Micrometer 8 is calibrated thus defining a zero gap between upper glass electrode 18 and lower glass electrode 19. Traveller 4 is lifted and locked into a secure position with clamp 2, thus separating lower cell assembly 41 from upper cell assembly 40. Micrometer 8 is then used to set a pre-defined gap between upper glass electrode 18 and lower glass electrode 19 by acting as a stop for traveller 4. A small controlled portion of the highly concentrated, and highly viscous liquid dispersion of charged particles is placed on surface of glass electrode 19. Clamp 2 is released and traveller 4 is lowered such that glass electrode 18 is made to urge against glass electrode 19 with the liquid toner therebetween, to the set gap as defined by micrometer 8. Electrical connector 17 is attached to interface/power supply (not shown) and electrical connector 18 is attached to interface/power supply (not shown) while infra-red LED and detector 6 and 10 are connected to interface/power supply (not shown). A voltage signal of any required profile is sent from the computer to interface/power supply to the electrical connectors 17 and 18 while current and optical sensors signals from 6 and 10 are being synchronously received by interface/power supply with subsequent transfer to computer (not shown) for processing.

Control electronics and software have been developed to be used in conjunction with the electrophoretic device. The electronics consisting of three distinct parts. Part one being an ISA (Industry Standard Architecture) bus board. This board is fitted into an ISA bus slot of the controlling computer; such a direct connection allowing for fast access and processing, thus supporting a minimal cell sampling time of at least 5 $\mu$s. The ISA board contains the digital storage and processing, D/A and A/D conversions, FIFO (first in first out) memory, control logic and optical sensor LED drivers. Part two consists of an interface. The interface contains the current amplifier, two optical detector amplifiers and the high voltage monitor amplifier. The third part of the electronics consists of the high voltage amplifier and power supply.

Circuit operation consisting of the downloading of software generated waveforms into FIFO memory in the ISA board. On command from the software the waveform is read from memory and is D/A converted and fed via the Interface to the high voltage amplifier. The high voltage waveform is then fed to the cell. A sample of the high voltage waveform is fed back to the ISA board via a buffer amplifier in the interface, and is A/D converted and stored into another FIFO memory location synchronous to the digital waveform source. The cell current returns to a current to voltage translator in the Interface, having a logarithmic gain function to allow for good resolution over a wide range of currents. This voltage translated current is A/D converted and loaded to separate FIFO memory, synchronous to the digital waveform source.

For optical sensing, on the ISA board the LED driver logic develops a train of short duration pulses from the reference crystal oscillator having a large mark-space ratio. These pulses are used to drive the infra-red LED's. The resultant infra-red pulse is reflected by toner marking particles adjacent to the inner surface of the glass electrodes and detected by the phototransistor detector. The change in optical density resulting from compaction or diffusion of the marking particles on the inner surface of the appropriate glass electrode surface, due to electrophoresis, is responsible for changing the light scattering mechanism and, hence, affecting the reflected light intensity registered by the optical detectors. The sensor detector signals are then fed back to the ISA board via amplifiers in the Interface. In the ISA board the signals are sampled during the pulse duration, A/D converted and stored into FIFO memory.

On board logic and memory sequence timing is managed by two PLD's (programmable logic devices). At the termination of a measurement, data representing voltage, current, and sensor outputs are stored in FIFO memory locations. Software will synchronously read out the parameters for graphical analysis.

It has been established that liquid toner sample conductivity, capacitance, mobility, zeta potential, Q/M, electrical stability and toner compaction are only some of the possible values that can be validly assessed from the current sensor and optical sensor data using known calculation methods.

Optical transients enable the derivation of electrophoretic mobility by sensing the arrival time of charged marking particles to either of the cell electrodes. The presence of identical optical emitter-detectors on the surface of both top and bottom electrodes of the cell allows the determination of mobility and any occurrence of both positively and negatively charged toner particles in the liquid toner dispersion. The particle arrival time is determined at the moment when particle density, occurring as a result of particle compaction due to electrophoresis, reaches saturation.

Due to the fast sampling rate of the electronics, in the order of about 5□s, very precise sampling data is possible. This feature allows the measurement of the current contribution from marking particles and other charge carriers with a wide range of mobility. In other words, both very fast charge carriers like, for example, micelles, and very slow marking particles are distinguishable, by an evaluation of both current and optical data which has been synchronously obtained. Also, the ability to apply very high electric fields, in the order of about $10^8$ V/m, to a toner sample in the cell permits evaluation of transient times for groups of both fast and slow charge carriers.

It is well known that liquid toner electrical properties can degrade under the subjection of high electric fields. These changes in electrical properties occurring to the liquid developer are sometimes referred to as electrical fatigue. This electrical fatigue of the liquid toner can be determined in this cell, by the application of positive and negative pulse voltages to the cell in a cyclic fashion, and due to the fact that the current response is digitally recorded at every cycle, any changes in liquid toner conductivity can be monitored as a function of the number of cycles. In this way it is possible to determined the liquid toners durability to withstand an intense electrical field and hence determining its electrical stability. This measurement has been found useful in mimicking accelerated age testing and also determining the expected life-cycle of the liquid developer in terms of continual use in a recycling environment, as well as providing a further means whereby toner characterisation can occur.

It has been found that the monitored change of capacitance associated with the electrophoretic mobility of the suspended particles provides an important and useful measure of characterising the particle suspension and hence liquid toner performance in an electrographic system.

During the cell test, there is a gradual build-up of the toner particles on one of the electrodes commensurate with the sign of their charge. This build-up in toner particles occurring to the surface of one of the cell electrodes, increases in thickness with time, and having an insulating dielectric nature, causes a change in the overall capacitance of the toner cell. This change in capacitance can be used to characterise the toner particles.

It has also been surprisingly found that toner compaction or adhesion can be readily determined with this cell. This type of measurement, with highly viscous and highly concentrated liquid toners, can not be readily conducted with the hitherto prior art. The time taken for marking particles compacted on one electrode, to fully diffuse and move to the oppositely charged electrode by application of a voltage, is synchronously measured both electrically and optically and the degree of toner compaction derived from these measurements.

The sensitivity of the gallium arsenide infra-red emitting diode and the spectrally matched silicon phototransistor detector of the present embodiment, at short distances to a reflective surface, allows the precise measurement of any change in optical density, compaction or diffusion of the marking particles, which are in turn responsible for changing the light scattering mechanism and, hence, affecting the reflected light intensity registered by the optical detectors. The measurement area being adjacent the inner surfaces of the glass electrodes and focused at a point equal to the maximum detector current output. The use of such an infra-red LED and spectrally matched detector minimises any dark currents, that is, residual or background currents due to non-incident illumination, and thus contributing to a high signal to noise ratio.

The following example demonstrates some of the possible electrical parameters obtainable from a particle suspension with the present invention, without any intention of being limited thereby.

A liquid toner with a solids content of 25% by weight and a high shear rate viscosity of 410 mPa·s was used in the illustrating example. Table 1 shows the basic set-up parameters for the cell.

TABLE 1

| | |
|---|---|
| Electrode Spacing | 50 □m |
| Sampling Rate | 40 □s |
| Voltage signal (DC) | −200 V |
| Electric Field | $4 \times 10^6$ V/m |

Figure 4:
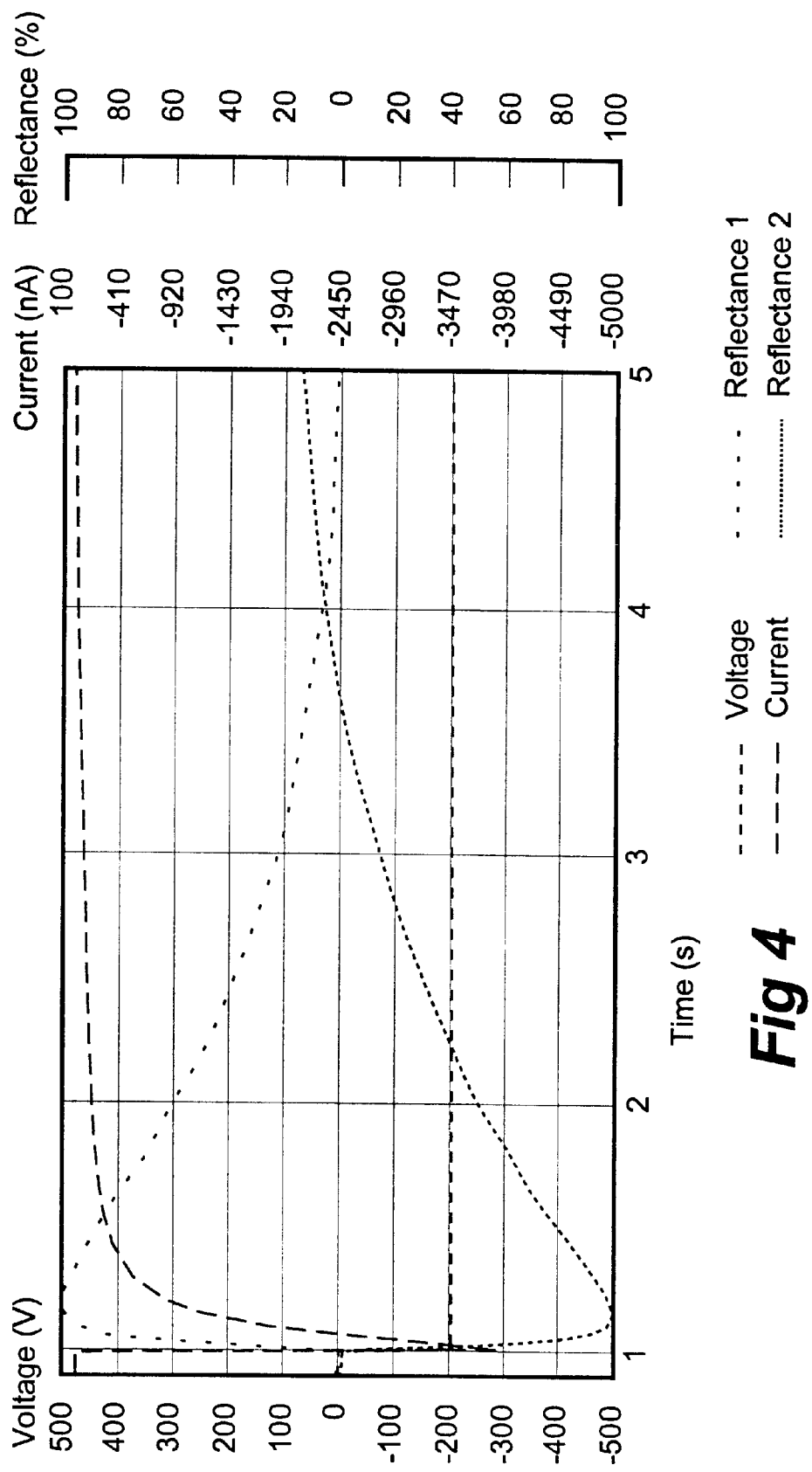
FIG. 4 is a graph of one example of use of the cell according to the present invention and shows typical out-put of synchronous optical and electrical readings.

The raw results of a typical output of selected synchronous electrical and optical measurements from the cell in the example are shown in FIG. 4. The cell was loaded with the liquid toner sample, and allowed to sit in the cell for approximately 2–3 minutes to ensure that any trapped air in the cell assembly had been fully displaced by the toner and that the fluid had become stationary. After a one second time interval from the application of a zero voltage signal across the cell electrodes, a step voltage of −200 V was applied. The displacement current and optical reflectance data was then recorded synchronously with the applied voltage signal. It should be noted that both Reflectance 1 and Reflectance 2 curves in FIG. 4 are represented by the differentials of the optical reflectance signals. As can be seen from FIG. 4, following the application of −200 V across the cell electrodes, the displacement current immediately dips to approximately −3800 nA and then steadily rises to level off at about 2 seconds to a constant value associated with the background current of so-called excess ions in the toner sample. It should also be noted that approximately within one second after the voltage is applied, the total displacement of charged particles has substantially occurred. The reflectance change at one electrode (Reflectance 1) initially rises quickly and then levels off, and then drops slightly. The reflectance change at the other electrode (Reflectance 2) mirrors the reflectance at the first electrode by initially falling quickly and then levels off and then rises. The initial rise and fall of the reflectance change at the respective first and second electrodes occurs during the period of maximum change in displacement current. It should also be noted that the transient time for the change in reflectance is used for further derivation of the electrophoretic mobility of toner particles, that is, the transient time for the reflectance change to reach a maximal value is utilised.

Table 2 illustrates some of the so obtained measured values as described in the above specification. Methods used in calculating the values illustrated in Table 2 are published and well know by those skilled in the art.

TABLE 2

| Mobility | $6.7 \times 10^{-11}$ m$^2$/V/s |
|---|---|
| Conductivity | 21.4 pS/cm |
| Zeta Potential | 125 mV |
| Q/M | 98 $\mu$C/g |
| $\Delta$ Capacitance | 0.24 pF |
| Stability ($\Delta$ Conductivity) | <0.05 pS/cm |

There has been hereto described a novel apparatus and method of determining the electrophoretic mobility, toner compaction and other pertinent electrical parameters deemed of importance to liquid toners in the art of electrostatography and which significantly influence the quality of a printed image. The instant invention allows the use of working strength dispersions of marking particles in liquids having a viscosity, in the order of up to 10,000 mPa·s, and a solids content of the marking particles, of up to 60% by weight therein without the need for dilution or any other preparation prior to measurement, by the use of high speed synchronously recorded electrical and optical data with an oppositely arranged pair of infra-red emitting diode and spectrally matched silicon phototransistor detector mounted side by side on parallel axes, as well as with high speed current sensing means. The present invention allows the replication of real conditions in an electrostatic printing or copying environment, including those of development gap, development speed and liquid toner stability over time including electrical stability and life expectancy in an electrographic printing or copying system.

The novel method and apparatus described can be used as an analytical tool, or as a tool for quality control in a manufacturing field. Further, use of the invention as an in-line measurement and control means within a printing or copying process is also envisaged.

It can be appreciated that changes to any of the above embodiments can be made without departing from the scope of the present invention and that other variations of the specific construction disclosed herein can be made by those skilled in the art without departing from the invention as defined in the appended claims.

The claims defining the invention are as follows:

1. A toner characterisation cell adapted to determine characteristics of insoluble particles in a liquid medium, the cell including a first electrode and a second electrode spaced apart by a selected gap, means to provide an electric field between the first electrode and the second electrode, means to measure a displacement current between the first electrode and the second electrode, first and second optical density measuring devices adapted to measure the change in optical density in the cell adjacent each electrode, and means to determine the characteristics from the displacement current and the change in optical density.

2. A toner characterisation cell as in claim 1 where the first electrode and the second electrode are substantially transparent or translucent.

3. A toner characterisation cell as in claim 1 wherein the electrodes are substantially planar.

4. A toner characterisation cell as in claim 1 wherein the electrodes are coated with a transparent conductive material.

5. A toner characterisation cell as in claim 1 wherein the electrodes are coated with conductive indium tin oxide.

6. A toner characterization cell as in claim 5, wherein the indium tin oxide is coated on a front surface of the electrodes.

7. A toner characterisation cell as in any one previous claim wherein the electrodes are formed from glass plates.

8. A toner characterisation cell as in claim 1 wherein the optical density measuring devices each comprise an infrared emitting diode and phototransistor pair.

9. A toner characterisation cell as in claim 1 wherein the selected gap is in the range of 1 $\mu$m to 10 mm.

10. A toner characterisation cell as in claim 1 further including micrometer means to adjust and measure the gap between the first electrode and the second electrode.

11. A particle mobility cell adapted to determine the mobility of an insoluble particle in a liquid medium, the cell including a first electrode and a second electrode spaced apart by a selected gap, means to provide an electric field between the first electrode and the second electrode, means to measure a displacement current between the first electrode and the second electrode, first and second optical density measuring devices adapted to measure the change in optical density in the cell adjacent each electrode, and means to determine the particle mobility from the displacement current and the change in optical density.

12. A particle mobility cell as in claim 11 where the first electrode and the second electrode are substantially transparent or translucent.

13. A particle mobility cell as in claim 11 wherein the electrodes are substantially planar.

14. A particle mobility cell as in claim 11 wherein the electrodes are coated with a transparent conductive material.

15. A particle mobility cell as in claim 11 wherein the electrodes are coated with conductive indium tin oxide.

16. A particle mobility cell as in claim 15 wherein the indium tin oxide is coated on a front surface of the electrodes.

17. A particle mobility cell as in claim 11 wherein the electrodes are formed from glass plates.

18. A particle mobility cell as in claim 11 wherein the optical density measuring devices each comprise an infrared emitting diode and phototransistor pair.

19. A particle mobility cell as in claim 11 wherein the gap is in the range of 1 $\mu$m to 10 mm.

20. A particle mobility cell as in claim 11 further including micrometer means to adjust and measure the gap between the first electrode and the second electrode.

21. An electrophoretic cell including a base, a tool post mounted to the base, a longitudinal track on the tool post, a traveller on the track, a first electrode assembly mounted to the base, a second electrode assembly mounted to the traveller, displacement adjustment means between the post and the traveller whereby the distance between the first electrode assembly and the second electrode assembly may be adjusted, a first optical density measuring device associated with the first electrode assembly, a second optical density measuring device associated with the second electrode, means to provide an electric field between the first electrode and the second electrode, means to determine a displacement current between the first electrode and the second electrode, and means to calculate electrophoretic characteristics of a suspension of particles in a highly viscous dispersion placed between the first and second electrodes from the displacement current and the change in optical density at the first and/or the second electrodes determined with the optical density measuring devices.

22. An electrophoretic cell as in claim 21 wherein the displacement adjustment means is a micrometer means.

23. An electrophoretic cell as in claim 21 where the first electrode assembly and the second electrode assembly are substantially transparent or translucent.

24. An electrophoretic cell as in claim 21 wherein the electrode assemblies are substantially planar.

25. An electrophoretic cell as in claim 21 wherein the electrode assemblies are coated with a transparent conductive material.

26. An electrophoretic cell as in claim 21 wherein the electrode assemblies are coated with conductive indium tin oxide.

27. An electrophoretic cell as in claim 26 wherein the indium tin oxide is coated on a front surface of the electrode assemblies.

28. An electrophoretic cell as in claim 21 wherein the electrode assemblies are formed from glass plates.

29. An electrophoretic cell as in claim 21 wherein the optical density measuring devices each comprise an infrared emitting diode and phototransistor pair.

30. A method of determining the characteristics of particles in a dispersion, the method including the steps of causing particles to move in response to an applied electric field between a first electrode and a second electrode spaced apart by a selected distance, determining a displacement current caused by the particles so moved, determining by optical means particle compaction or diffusion due to the particle movement adjacent the first and/or second electrodes and determining the characteristics from the displacement current and the change in particle compaction or diffusion.

31. A method of determining the characteristics of particles in a dispersion as in claim 30 wherein the displacement current and the particle compaction or diffusion are measured synchronously.

32. A method of determining the mobility of particles in a liquid dispersion, the method including the steps of placing a selected amount of the liquid with the particles suspended therein on to a first planar transparent electrode, moving a second planar transparent electrode adjacent the first electrode such that they are spaced apart by a selected gap, applying a selected voltage to one of the electrodes to cause particles to move electrophoretically between the first electrode and the second electrode, measuring a displacement current caused by the particles so moved, determining by optical means particle compaction or diffusion due to the particle movement adjacent the first and/or second electrode and calculating the particle mobility from the displacement current and the observed changes in optical density.

33. A method of determining the mobility of particles in a liquid dispersion as in claim 32 wherein the displacement current and the particle compaction or diffusion are measured synchronously.

* * * * *